(12) United States Patent
Hashimoto et al.

(10) Patent No.: US 11,179,318 B2
(45) Date of Patent: Nov. 23, 2021

(54) COSMETIC COMPOSITION

(71) Applicant: NIPPON PAPER INDUSTRIES CO., LTD., Tokyo (JP)

(72) Inventors: Tadafumi Hashimoto, Tokyo (JP); Shinji Sugiyama, Tokyo (JP); Shinya Yamaguchi, Tokyo (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 3 days.

(21) Appl. No.: 16/930,492

(22) Filed: Jul. 16, 2020

(65) Prior Publication Data

US 2020/0345622 A1     Nov. 5, 2020

Related U.S. Application Data

(63) Continuation of application No. PCT/JP2019/001522, filed on Jan. 18, 2019.

(30) Foreign Application Priority Data

Jan. 19, 2018 (JP) .............................. JP2018-007388

(51) Int. Cl.
*A61K 8/00* (2006.01)
*A61K 8/9728* (2017.01)
*A61Q 1/12* (2006.01)

(52) U.S. Cl.
CPC .............. *A61K 8/9728* (2017.08); *A61Q 1/12* (2013.01); *A61K 2800/26* (2013.01); *A61K 2800/412* (2013.01)

(58) Field of Classification Search
CPC ............................. A61K 8/9728; A61K 35/66
See application file for complete search history.

(56) References Cited

U.S. PATENT DOCUMENTS

| 5,674,506 A | 10/1997 | So et al. |
| 5,968,811 A * | 10/1999 | Greenshields ......... C12N 1/063 435/255.2 |
| 2005/0025730 A1 | 2/2005 | Chevalier et al. |
| 2006/0110402 A1 | 5/2006 | Eguchi et al. |
| 2012/0070376 A1 * | 3/2012 | Ostroff ................. A61K 31/704 424/9.1 |

FOREIGN PATENT DOCUMENTS

| JP | 8-20513 | 1/1996 |
| JP | 11-501691 | 2/1999 |
| JP | 2002-370961 | 12/2002 |
| JP | 2004-107240 | 4/2004 |
| JP | 2005-15348 | 1/2005 |
| JP | 2005-53906 | 3/2005 |
| WO | 96/28476 | 9/1996 |
| WO | 2004/018650 | 3/2004 |

OTHER PUBLICATIONS

International Search Report, dated Mar. 5, 2019 in corresponding International Patent Application No. PCT/JP2019/001522.

* cited by examiner

*Primary Examiner* — Benjamin J Packard
(74) *Attorney, Agent, or Firm* — Wenderoth, Lind & Ponack, L.L.P.

(57) ABSTRACT

An object is to provide a cosmetic composition that: has a high soft focus effect, a high skin beautifying effect, and a high moisture retaining effect; is safe; and enables reduction in environmental impact.
Yeast cell wall particles retaining shapes of yeast cell walls and having an average particle diameter ranging from 1 to 25 μm are prepared and blended in a cosmetic composition.

14 Claims, 5 Drawing Sheets

COSMETIC COMPOSITION

CROSS-REFERENCE TO RELATED APPLICATIONS

This application is based upon and claims the benefits of priorities from Japanese Patent Application No. 2018-007388, filed Jan. 19, 2018; and International Application No. PCT/JP2019/001522, filed Jan. 18, 2019, the entire contents of which are incorporated herein by reference.

TECHNICAL FIELD

The present invention relates to a cosmetic composition, and particularly, to a powder composition of a material derived from yeast and a cosmetic composition containing the powder composition.

BACKGROUND ART

Makeup cosmetics, such as foundation, makeup bases, and face powder, are used to make skin look beautiful. Makeup cosmetics are expected to have an important role of: covering dullness caused by poor blood circulation and pigmentation of skin; and blurring unevenness and wrinkles on skin by scattered reflection of light to make skin defects inconspicuous and enhance the transparency and bare skin look. The use of scattered reflection of light to blur unevenness and wrinkles on skin is called a soft focus effect.

Use of a filler to obtain a soft focus effect has been known, conventionally, the filler being, for example: an inorganic powder material, such as silica, alumina, mica, or titanium oxide; or an organic powder material derived from fossil fuels, such as polyethylene powder (Patent Literature 1).

Furthermore, mixing β-glucan derived from microorganisms, such as yeast, into skin cosmetics has been proposed, for skin moisture retention, anti-aging, and a skin beautifying effect (Patent Literature 2).

Research and development on various uses of yeast as a biological material have been conducted, and use of a decolorized yeast cell wall fraction as a coating agent or a coating film has also been proposed (Patent Literature 3).

CITATION LIST

Patent Literature

Patent Literature 1: Japanese Patent Application Laid-open Publication No. 2005-53906
Patent Literature 2: Japanese Patent Application Laid-open Publication No. 2005-15348
Patent Literature 3: International Publication No. WO 2004/018650

SUMMARY OF INVENTION

Technical Problem

Cosmetics containing inorganic powder materials, such as titanium oxide, have a drawback of tending to cause makeup films to be in a matte state without luster and skin to look dull. Furthermore, there is a concern that cosmetics containing organic powder materials derived from fossil fuels, such as polyethylene powder, may adversely affect the environment when used in large quantities because the organic powder materials do not have biodegradability. In recent years, social awareness about environmental conservation and sustainable development is increasing and biological materials that are environmentally friendly are thus expected to be used.

In view of the foregoing, an object of the present invention is to provide a cosmetic composition that: has a high soft focus effect, a high skin beautifying effect, and a high moisture retaining effect; is safe; and enables reduction in environmental impact.

Solution to Problem

Inventors of the present invention have conducted research diligently, have found out that using given yeast particles enables provision of a cosmetic composition excellent in various respects, such as its soft focus effect, and have completed the present invention described below.

[1] A cosmetic composition comprising: yeast cell wall particles retaining shapes of yeast cell walls and having an average particle diameter ranging from 1 to 25 μm.

[2] The cosmetic composition according to the above item [1], wherein the yeast cell wall particles are a cell wall fraction that has intracellular components of yeast removed.

[3] The cosmetic composition according to the above items [1] or [2], wherein
when a flat layer is formed of powder of the yeast cell wall particles, the flat layer has a reflectance satisfying one or both of:
a condition (a) where the reflectance is 30% or less at an incident angle of 20°; and
a condition (b) where the reflectance is 30% or less at an incident angle of 60°.

[4] The cosmetic composition according to any one of the above items [1] to [3], wherein the cosmetic composition is a makeup cosmetic material.

[5] The cosmetic composition according to any one of the above items [1] to [4], wherein the cosmetic composition is a powder cosmetic material.

[6] A powder composition for enhancing a soft focus effect, comprising: yeast cell wall particles retaining shapes of yeast cell walls.

Advantageous Effects of Invention

According to the present invention, a cosmetic composition is able to be provided, the cosmetic composition: having a high soft focus effect, a high skin beautifying effect, and a high moisture retaining effect; being safe; and also enabling reduction in environmental impact.

DESCRIPTION OF EMBODIMENTS

Figure 1:
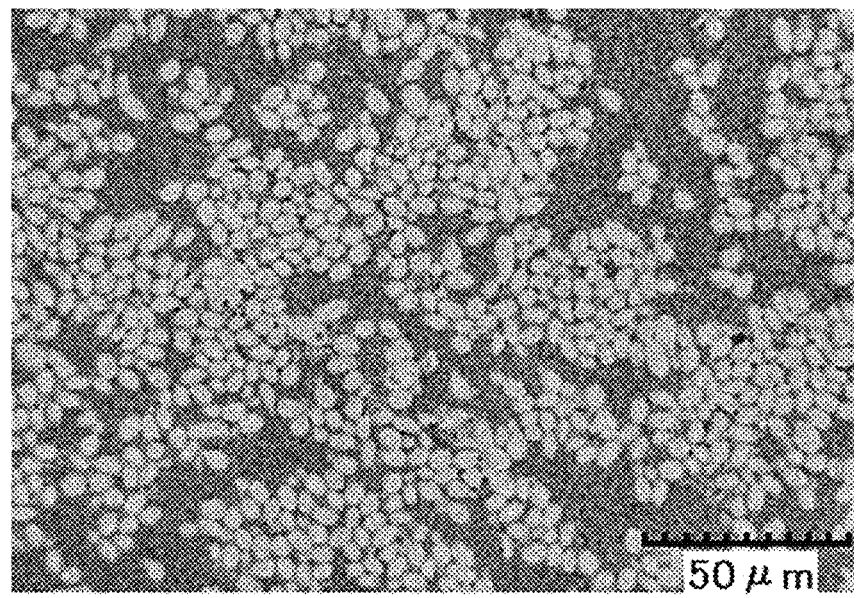
FIG. 1 is a micrograph of yeast cell wall fraction particles of Production Example 1.

Embodiments of the present invention will be described hereinafter. Unless otherwise specified, the phrase "ranging from AA to BB" means "being in the range of AA or more and BB or less" (where "AA" and "BB" represent arbitrary numerical values).

Yeast Cell Wall Particle

A cosmetic composition of the present invention contains yeast cell wall particles. According to the present invention, the term "yeast cell wall particle" means a particle formed of a cell wall of yeast.

The yeast cell wall particles used in the present invention retain shapes of the yeast cell walls. "Retaining a shape of a yeast cell wall" means that the outer shape of the cell wall has been retained when the shape of the particle is observed as a whole, such that the outer shape of the cell wall is the same as or similar to that of the overall shape of a viable cell of yeast, without the cell wall being in a destroyed state where the cell wall has been crushed or ground and the outer shape of yeast has not been maintained. Therefore, the yeast cell wall particles used in the present invention have substantially the same outer shape as or similar outer shape to their viable cells of yeast.

An average particle diameter of the yeast cell wall particles may be used as an index of whether or not the shapes of the cell walls of the yeast cell wall particles have been retained. The upper limit of the average particle diameter of the yeast cell wall particles used in the present invention is 25 µm or less, preferably 20 µm or less, and more preferably 15 µm or less. On the other hand, the lower limit of the average particle diameter is 1 µm or more, preferably 3 µm or more, and more preferably 5 µm or more. If chemical or physical treatment (described in detail below) for removing intracellular components or the like of yeast is too severe, the yeast is likely to aggregate or the outer shape of the yeast is unable to be retained, and the average particle diameter of the yeast cell wall particles tends to be outside the ranges between the above upper and lower limits.

The average particle diameter disclosed according to the present invention is able to be determined by, for example, a particle diameter at a cumulative total of 50% by measurement using a laser diffraction particle size distribution analyzer (for example, Mastersizer 3000, manufactured by Malvern), using water as a dispersion medium for measurement, and adding about 0.1 g of a sample.

Retaining the shapes of the yeast cell walls and blending the yeast cell wall particles having the above average particle diameter in a cosmetic composition enables formation of a cosmetic composition having a high soft focus effect. Although the mechanism of this action is not fully clear, it is presumed that the above-mentioned predetermined shape and size contribute to favorable light scattering. Since the yeast cell wall particles are a natural material, and the sizes, such as the average particle diameters, of the yeast cells vary due to individual difference of each yeast cell, it is also presumed that appropriate variation of the sizes of the yeast cell wall particles contributes to favorable light scattering. It is also presumed that retaining the shapes of the yeast cell walls and blending the yeast cell wall particles having the above average particle diameter in a cosmetic composition enable unevenness and wrinkles on the skin to be filled adequately therewith, reduce dullness caused by shade, and thus enable formation of a cosmetic composition having a high skin beautifying effect.

In the present invention, planar shapes of the yeast cell wall particles are preferably oval. The "planar shape" means a two-dimensional shape of an object when the object is viewed along a normal line to a plane tangent to the object (that is, a tangent plane). Therefore, according to the present invention, the planar shape of a yeast cell wall particle means a two-dimensional shape of the yeast cell wall particle when the yeast cell wall particle is viewed along a normal line to a tangent plane to the outermost shell of the yeast cell wall particle. That is, a preferable yeast cell wall particle of the present invention has an oval planar shape when the yeast cell particle is viewed along a normal line to at least one tangent plane tangent to the outermost shell of the yeast cell wall particle (for example, a tangent plane parallel to the major axis of the particle).

According to the present invention, the term "oval" means oval or curved like an oval, and includes being egg-shaped, being rice grain-shaped (where "rice" includes short grain rice, medium grain rice, and long grain rice), and being oblong. Furthermore, an "oval" shape may include a straight line portion in a part of its curved shape, and for example, includes a rounded rectangle. An oval yeast cell wall particle used in the present invention preferably has a line symmetry axis that is bilaterally symmetric at at least one position in its oval planar shape, but may have a bilaterally asymmetric shape without a geometrically strict line symmetry axis.

Sphericity of the yeast cell wall particles used in the present invention is usually in the range of 0.1 or more and less than 1.0, and preferably in the range of 0.4 or more and less than 1.0, since the shapes of the yeast cell walls are retained.

The soft focus effect can be enhanced even more by the non-sphericalness of the yeast cell wall particles having the oval planar shape or having their sphericity or the like adjusted to an appropriate range. Although the mechanism of this action is not fully clear, it is presumed that having such a shape contributes to favorable light scattering or achieves a soft focus effect for blurring shade caused by unevenness.

Any type of yeast may be employed for use in the present invention without any particular limitation as long as the above-mentioned geometric conditions are satisfied. Types of yeast that may be employed include ascospore yeasts and asporogenous yeasts. Specific examples of the yeast include the following types.

Examples of the ascospore yeasts may include those belonging to the genus *Shizosaccharomyces*, the genus *Saccharomyces*, the genus *Kluyveromyces*, the genus *Hansenula*, the genus *Pichia*, the genus *Debaryomyces*, and the genus *Lipomyces*; and more specifically may include: *Shizosaccharomyces pombe, Shizosaccharomyces octosporus; Saccharomyces cerevisiae, Saccharomyces uvarum, Saccharomyces rouxii; Kluyveromyces fragilis, Kluyveromyces lactis; Hansenula anomala; Pichia membranaefaciens; Debaryomyces hansenii*; and *Lipomyces starkeyi*.

Examples of the asporogenous yeasts may include those belonging to the genus *Torulopsis*, the genus *Candida*, and the genus *Rhodotorula*; and more specifically may include: *Torulopsis versatilis; Candida tropicalis, Candida lipolytica, Candida utilis*; and *Rhodotorula glutinis*.

In terms of the shape, retention of the shape, size, or safety, the types of yeast used in the present invention may preferably include brewer's yeast, wine yeast, baker's yeast, and torula yeast, and specifically may include *Saccharomyces cerevisiae, Saccharomyces uvarum, Saccharomyces rouxii, Kluyveromyces fragilis, Torulopsis versatilis, Candida tropicalis, Candida lipopolytica, Candida utilis*, and *Rhodotorula glutinis*.

The yeast cell wall particles are allowable if they retain their shapes of yeast cell walls, and may be, for example, those resulting from drying of viable cells of yeast. A cell wall fraction obtained by removal of intracellular components from yeast may be preferably used as the yeast cell wall particles. An "intracellular component" refers to a cytoplasmic matrix, an organelle, a nucleus, a granule, or the like existing in a cell, and materially includes components, such as nucleic acids, lipids, and proteins, for example. Furthermore, the yeast cell wall particles may further have their cell membranes removed therefrom.

A yeast cell wall is composed of plural layers, and contains components, such as β-glucan, chitin, and mannoprotein. Removing the intracellular components and the like enables content ratios of these components in the yeast cell wall particles to be increased. Furthermore, in one embodiment of the yeast cell wall particles of the present invention, those obtained by removal of mannoprotein from the multilayered cell walls are more suitable as a component to be added to a cosmetic composition. Generally, a cell wall of yeast has layers mainly composed of mannoprotein respectively present at a surface nearer to the inside of the yeast cell and a surface nearer to the outer shell of the yeast cell, and a layer mainly composed of β-glucan and a layer mainly composed of β-glucan and chitin are sandwiched between these two layers of mannoprotein. Intracellular components and mannoprotein are preferably removed in terms of color and preservation stability of the cosmetic composition. A yeast cell wall particle from which at least intracellular components have been removed as described above is referred to as an "yeast cell wall fraction particle." The "yeast cell wall fraction particle" also includes a particle in a form from which a cell membrane or a mannoprotein layer has been removed. (The "yeast cell wall fraction particle" is a form encompassed by the "yeast cell wall particle," and unless otherwise specified below, the term "yeast cell wall particle" includes the concept of the "yeast cell wall fraction particle.")

The upper limit of β-glucan content in the yeast cell wall particles is not particularly limited, but may be usually 90% by weight, 80% by weight, 75% by weight, or 70% by weight or less due to the composition of the cell wall components. The lower limit of β-glucan content in the yeast cell wall particles is preferably 5% by weight or more, more preferably 10% by weight or more, even more preferably 15% by weight or more, and particularly preferably 20% by weight. Setting the lower limit of the β-glucan content in this manner enables enhancement of the moisture retaining property of a cosmetic composition when the particles are blended in the cosmetic composition. As described above, one example of a method of obtaining yeast cell wall particles having a high β-glucan content may include removing intracellular components. Furthermore, the β-glucan content may be further increased by further removal of a mannoprotein layer. That is, the yeast cell wall fraction particles may be used as β-glucan-rich particles.

Dry yeast powder may have a color, such as a yellowish color. The yeast cell wall particles used in a cosmetic composition are preferably white. The lower limit of whiteness of the yeast cell wall particles in the present invention is preferably 75 or more, more preferably 80 or more, and even more preferably 85 or more. On the other hand, the upper limit of the whiteness is not particularly limited according to the present invention, but is preferably 100 in theory, and is usually about 98, 95, 93, or 90.

Preferred yeast cell wall particles may be defined by a reflectance measured under predetermined conditions, the reflectance serving as an index. A preferred embodiment of the yeast cell wall particles may be defined as described below, for example, by use of a reflectance obtained by a reflectance measurement method described with respect to Examples below. As will be described in detail with respect to Examples below, values of reflectance referred to in the description of the present invention are reflectances that are able to be relatively determined on the basis of the case for soft flour of wheat.

When Incident Angle is 20° The upper limit of the reflectance is preferably 30% or less, more preferably 20% or less, and even more preferably 10% or less. The lower limit of the reflectance is preferably larger than 0%, and more preferably 1% or more.

When Incident Angle is 60°

The upper limit of the reflectance is preferably 30% or less, more preferably 20% or less, and even more preferably 10% or less. The lower limit of the reflectance is preferably larger than 0%, and more preferably 1% or more.

The reflectance is preferably in the above-mentioned suitable range for when the incident angle is 20° or the above-mentioned suitable range for when the incident angle is 60°, and is more preferably in the above-mentioned suitable ranges for both when the incident angle is 20° and when the incident angle is 60°. It is considered that the reflectance in the above-described ranges prevents too much gloss and luster and contributes to provoking the soft focus effect.

Methods for the removal of the intracellular components, the removal of the cell membrane, and the removal of the mannoprotein layer are not particularly limited as long as the outer shape of the cell wall is able to be retained. An example of a method of removing the intracellular components may include: damaging a part of the cell walls so as not to spoil the outer shapes of the cell walls, chemically by use of an enzyme or a chemical or physically by use of an ultrasonic crusher or the like; and then washing these cells to extract the intracellular components with water or a solvent in which the cytoplasm is soluble. A generally known method of extracting an yeast extract may be used as long as care is taken to damage the cell walls without spoiling the outer shape. That is, a residue obtained after extraction of the yeast intracellular components may be recovered, the residue serving as the yeast cell wall fraction particles. For example, yeast may be soaked in hot water to extract the intracellular components. The yeast from which the intracellular components have been removed can also be purchased as a commercial product.

The mannoprotein layer can be removed by subjecting the yeast from which the intracellular components have been removed as described above further to oxidative decomposition treatment with an oxidizing agent, such as hydrogen peroxide, hypochlorous acid, or ozone. Removing the mannoprotein layer enables the β-glucan content in the yeast cell wall particles to be relatively increased.

Furthermore, the treatment with the oxidizing agent, such as hydrogen peroxide, hypochlorous acid, or ozone, also enables decolorization of the yeast cell wall particles. Therefore, whiteness of the yeast cell wall particles is able to be increased by the treatment with the oxidizing agent.

Cell membranes are usually damaged in the process of extracting the intracellular components or the process of removing mannoprotein, and thus most of the cell membranes may be removed by these processes. Preferably, delipidation treatment may be further performed to remove any remaining lipid components derived from the cell membranes or the like. A general method used for microorganisms, such as yeast, may be employed for the delipidation treatment. For example, after extracting the intracellular components, alcohol extraction or acetone extraction may be performed, where the alcohol extraction is more preferable. Examples of the alcohol may include: alcohol, and an aqueous alcohol solution; preferably a lower alcohol, such as ethanol, methanol, and butanol; and more preferably ethanol. Performing the delipidation treatment enables the f-glucan content of the yeast cell wall particles to be relatively increased and change of color and odor to be reduced.

Surfaces of the yeast cell wall particles may be treated with a surface treatment agent. Examples of the surface treatment agent may include one or two or more selected from: fluorinated compounds; silicone compounds; metal soaps; lecithin; hydrogenated lecithin; collagen; hydrocarbons, higher fatty acids; higher alcohols; esters; waxes; waxy substances; and surfactants.

The yeast cell wall particles used in the present invention are able to enhance the soft focus effect and skin beautifying effect. Furthermore, the yeast cell walls contain β-glucan that is an excellent component for imparting a moisture retaining property. Yeasts are materials derived from natural materials that can be used in products, such as foods. Therefore, the yeast cell wall particles serve as a safe component to be blended in cosmetic compositions, and are a material that enables reduction in environmental impact since the yeast cell wall particles are biodegradable.

The yeast cell wall fraction particles, which are a preferable embodiment of the yeast cell wall particles, have a higher β-glucan content and a more excellent moisture retaining property. Furthermore, they are a more excellent component to be blended in cosmetic compositions in terms of preservation stability and the like, since the cytoplasmic matrices, organelles, and the like have been removed therefrom.

The above-described yeast cell wall particles may also be used as a powder composition for enhancing the soft focus effect in technical fields other than cosmetic applications.

Cosmetic Composition

A cosmetic composition of the present invention contains the above-described yeast cell wall particles. The cosmetic composition of the present invention can be obtained, for example, by blending the yeast cell wall particles in a cosmetic composition and stirring and mixing the cosmetic composition.

The amount of the yeast cell wall particles blended in the cosmetic composition of the present invention may be appropriately adjusted according to the use, form, and the like of the cosmetic composition. The upper limit of amount of the yeast cell wall particles blended is not particularly limited in terms of the effects of the present invention, but generally, the upper limit of mixture of powder into cosmetics may be, for example, 90% by weight or less, 70% by weight or less, or 50% by weight or less. Furthermore, for sufficient dispersion in cosmetics having components other than the yeast cell wall particles, the components serving as main dispersion media, the upper limit of the amount blended may be preferably 30% by weight or less, more preferably 25% by weight or less, and even more preferably 20% by weight. On the other hand, the lower limit of amount of the yeast cell wall particles blended is preferably 5% by weight or more, more preferably 10% by weight or more, and even more preferably 15% or more. Setting the lower limit of the amount blended as described above enables provision of a cosmetic composition having a soft focus effect, a skin beautifying effect, and a moisture retaining property that are even more excellent.

Since the yeast cell wall particles have the above-mentioned properties, the cosmetic composition of the present invention is suitable for makeup cosmetics. The makeup cosmetics may be base makeup cosmetics or point makeup cosmetics. Examples of the base makeup cosmetics may include dusting powders, such as foundations and face powders. Examples of the point makeup cosmetics may include lipsticks, blushers, eyeliners, mascaras, eye shadows, eyebrow cosmetics, nail enamels, and nail treatments.

Preferable examples of the form of the makeup cosmetics according to the present invention may include that of powder cosmetics. The objective effects can be readily achieved by formation as powder cosmetics, such as loose powder, since there is no need to perform an emulsification step or press molding and there is thus no need to limit the amount of yeast cell wall particles blended for the purpose of having their forms maintained.

The cosmetic composition of the present invention contains the yeast cell wall particles, but other powder generally used for cosmetic components may be blended in the cosmetic composition, depending on conditions, such as the use of the cosmetic composition. Examples of the cosmetic powder may include inorganic powders, glittering powders, organic powders, pigment powders, metal powders, and composite powders.

More specifically, the following examples may be used.

Examples of white inorganic pigments may include titanium oxide, zinc oxide, cerium oxide, barium sulfate, talc, muscovite, phlogopite, lepidolite, biotite, synthetic mica, sericite, synthetic sericite, kaolin, silicon carbide, smectite, aluminum oxide, magnesium oxide, zirconium oxide, antimony oxide, diatomaceous earth, aluminum silicate, metasilicic acid aluminum magnesium, calcium silicate, barium silicate, magnesium silicate, calcium carbonate, magnesium carbonate, hydroxyapatite, boron nitride, and silicon dioxide.

Examples of colored inorganic pigments may include red ocher (Bengala), yellow iron oxide, black iron oxide, carbon black, black titanium oxide, chromium oxide, chromium hydroxide, prussian blue, and ultramarine blue.

Examples of glittering powders may include titanium dioxide-layered mica, titanium dioxide-coated synthetic phlogopite, titanium dioxide-coated bismuth oxychloride, iron oxide-coated mica, iron oxide-coated mica titanium, prussian blue-treated mica titanium, carmine-treated mica titanium, bismuth oxychloride, fish scale flake, titanium dioxide-coated glass powder, and aluminum powder.

Examples of organic polymer resin powders may include: glittering materials of resin-laminated powders, such as laminated powder of epoxy resin-coated polyethyleneterephthalate aluminum, polyethylene telephthalate-polyolefin laminated film powder, polyethylene terephthalate-polymethyl methacrylate laminated film powder, and laminated powder of epoxy resin-coated polyethyleneterephthalate aluminum; and further, polyamide resins, polyethylene resins, polyacrylic resins, polyester resins, fluororesins, cellulose resins, polystyrene resins, co-polymer resins, such as styrene-acryl copolymer resins, polypropylene resins, silicone resins, and urethane resins.

Examples of organic low molecular weight powders may include N-acyl lysine.

Examples of natural organic powders may include starch, silk powder, and cellulose powder.

Examples of organic pigment powders may include Red No. 3, Red No. 104, Red No. 106, Red No. 201, Red No.

202, Red No. 205, Red No. 226, Red No. 228, Orange No. 203, Orange No. 204, Orange No. 205 No. 1, Blue No. 1, Blue No. 404, Yellow No. 4, Yellow No. 5, Yellow No. 401, and Green No. 3.

Examples of the metal powders may include aluminum powder, gold powder, and silver powder.

Examples of the composite powders may include fine titanium oxide-coated mica titanium, fine zinc oxide-coated mica titanium, barium sulfate-coated mica titanium, titanium oxide-containing silicon dioxide, and zinc oxide-containing silicon dioxide.

The above-mentioned powders may be subjected to surface treatment with one or two or more selected from fluorinated compounds, silicone compounds, metal soaps, lecithin, hydrogenated lecithin, collagen, hydrocarbons, higher fatty acids, higher alcohols, esters, waxes, waxy substances, and surfactants.

The cosmetic composition of the present invention can be prepared by appropriately adding components generally used in cosmetics, such as oil components and emulsifiers, in addition to the yeast cell wall particles described above, depending on intended products.

Examples of the oil components used in cosmetics may include: hydrocarbons, such as liquid paraffin and squalane; natural animal and vegetable fats and oils, such as olive oil, jojoba oil, avocado oil, soybean oil, meadowfoam oil, and lanolin; fatty acid esters, such as 2-ethyl hexanoic acid cetyl, isononyl isononanoate, isotridecyl isononanoate, isopropyl myristate, isopropyl palmitate, 2-ethylhexyl palmitate, 2-ethylhexyl stearate, and stearyl stearate; triglycerides and fatty acid ester oils of polyhydric alcohols, such as caprylic/capric triglyceride and tri glyceryl(2-ethylhexanoate); higher alcohols, such as cetyl alcohol, stearyl alcohol, isostearyl alcohol, and behenyl alcohol; higher fatty acids, such as lauric acid, myristic acid, palmitic acid, stearic acid, and isostearic acid; chain silicone oils, such as dimethylpolysiloxane, and methylphenylpolysiloxane; cyclic silicone oils, such as decamethylcyclopentanesiloxane; and liquid or solid silicone oils, such as trimethyl siloxysilicic acid, silicone gel, and silicone powder. These oil components may be used alone or in combination of two or more.

Examples of the emulsifiers used in cosmetics may include anionic surfactants, cationic surfactants, amphoteric surfactants, nonionic surfactants, and silicone-based surfactants serving as emulsifiers for silicone oil, and may preferably include non-ionic surfactants and silicone-based surfactants. These may be used alone or in combination of two or more. Examples of nonionic surfactants may include polyoxyethylene castor oil, polyoxyethylene hydrogenated castor oil, and derivatives thereof; sorbitan fatty acid esters, such as sorbitan monopalmitate, sorbitan monostearate, sorbitan monooleate, sorbitan coconut fatty acid ester, sorbitan tristearate, and sorbitan trioleate; polyoxyethylene sorbitan fatty acid esters, such as polyoxyethylene sorbitan monolaurate, polyoxyethylene sorbitan monopalmitate, polyoxyethylene sorbitan monooleate, polyoxyethylene sorbitan tristearate, and polyoxyethylene trioleate; polyoxyethylene sorbitol monolaurate, and tetrastearic acid polyoxyethylene sorbitol fatty acid ester; glycerin fatty acid esters, such as glyceryl monostearate, glyceryl monostearate, self emulsification type glyceryl monostearate, and glyceryl monoisostearate; polyoxyethylene glycerin fatty acid esters, such as polyoxyethylene glyceryl monostearate, polyoxyethylene glyceryl monoisostearate, polyoxyethylene glyceryl tristearate, polyoxyethylene glyceryl triisostearate, and polyoxyethylene glyceryl trioleate; polyoxyethylene alkyl ethers, such as polyoxyethylene lauryl ether, polyoxyethylene cetyl ether, polyoxyethylene stearyl ether, polyoxyethylene oleyl ether, and polyoxyethylene octyldodecyl ether; polyethylene glycol fatty acid esters, such as polyethylene glycol monolaurate, and polyethylene glycol monooleate; polyethylene glycol fatty acid esters, such as polyethylene glycol monolaurate, and polyethylene glycol monooleate; and polyglycerin fatty acid esters, such as polyglyceryl monolaurate, polyglyceryl monomyristate, polyglyceryl monostearate, polyglyceryl monooleate, polyglyceryl tristearate, and polyglyceryl trioleate. Examples of the silicone surfactants may include polyether-modified silicone and polyglycerin-modified silicone.

The cosmetic composition of the present invention may contain components generally used in cosmetics, in addition to the above. For example, the cosmetic composition of the present invention may contain a polyhydric alcohol, a humectant, a saccharide, a preservative, an antibacterial agent, a sequestering agent, a polymer thickener, such as a water-soluble polymer, a lower alcohol, a film forming agent, a neutralizing agent, a pH adjuster, a powder component, or an ultraviolet absorber. Furthermore, for example, the cosmetic composition of the present invention may contain: another cosmetic or medicinal component, such as a vitamin, a skin activator, a blood circulation promoter, an anti-inflammatory agent, a whitening agent, or an anti-wrinkle component; a bioactive component; perfume; and/or a pigment.

Examples of the polyhydric alcohol may include 1,3-butylene glycol, dipropylene glycol, propylene glycol, glycerin, 1,2-pentanediol, isoprene glycol, polyethylene glycol, methyl glucoside, sorbitol, and diglycerin.

Examples of the humectant may include hyaluronic acid, collagen, elastin, sodium lactate, cyclodextrin, pyrrolidone carboxylic acid and salts thereof, and natural and synthetic ceramides.

Examples of the preservative and antibacterial agent may include benzoic acid, salicylic acid, carbolic acid, sorbic acid, para-hydroxybenzoic acid esters, para-chloromethcresol, hexachlorophene, benzalkonium chloride, chlorhexidine chloride, trichlorocarbanilide, photosensitizers, and phenoxyethanol.

Examples of the sequestering agent may include edetates, such as disodium ethylenediaminetetraacetate, edetic acid, and edetate sodium salt.

Examples of the water-soluble polymer or demulcent drug may include gum arabic, tragacanth gum, galactan, guar gum, carrageenan, pectin, agar, quince seed, dextran, dextrin, pullulan, carboxymethyl starch, collagen, casein, gelatin, methylcellulose, methyl hydroxypropylcellulose, hydroxyethylcellulose, hydroxypropylcellulose, sodium carboxymethylcellulose, sodium alginate, sodium carboxymethyldextran, carboxyvinyl polymer, and bentonite.

Examples of the film forming agent may include poly(alkyl acrylate), eicosene-vinyl pyrrolidone polymer, and ester gum.

Examples of the neutralizing agent may include potassium hydroxide, sodium hydroxide, triethanolamine, and sodium carbonate.

Examples of the pH adjuster may include lactic acid, citric acid, glycolic acid, succinic acid, tartaric acid, dl-malic acid, potassium carbonate, sodium hydrogen carbonate, and ammonium hydrogen carbonate.

Examples of the lower alcohol may include ethanol, and isopropanol.

Examples of the ultraviolet absorber may include: cinnamic acid-based ultraviolet absorbers, such as 2-ethylhexyl paramethoxycinnamate, hexyl 2-[4-(diethylamino)-2-hydroxybenzoyl]benzoate, benzyl paramethoxycinnamate, 2-ethoxyethyl paramethoxycinnamate, diparamethoxycinnamate glyceryl mono-2-ethylhexanoate, and a mixture of isopropyl paramethoxycinnamate diisopropyl cinnamic acid ester mixture; benzophenone ultraviolet absorbers, such as hydroxymethoxybenzophenone, hydroxymethoxybenzophenone sulfonic acid, sodium hydroxymethoxybenzophenone sulfonate, dihydroxymethoxybenzophenone, sodium dihydroxymethoxybenzophenone disulfonate, dihydroxybenzophenone, and tetrahydroxybenzophenone; benzoyl ester ultraviolet absorbers, such as para-aminobenzoic acid, ethyl para-aminobenzoate, glyceryl para-aminobenzoate, amyl para-dimethylaminobenzoate, octyl para-dimethylaminobenzoate, ethyl 4-[N,N-di(2-(hydroxypropyl)amino]benzoate, and 2-(4-diethylamino-2-hydroxybenzoyl) hexyl benzoate; salicylic acid-based ultraviolet absorbers, such as ethylene glycol salicylate, phenyl salicylate, octyl salicylate, benzyl salicylate, p-tert-butylphenyl salicylate, and homomenthyl salicylate; triazine-based ultraviolet absorbers, such as 2,4,6-trianilino-p-(carbo-2'-ethylhexyl-1'-oxy)-1,3,5-totriazine; and others, such as 4-tert-butyl-4'-methoxydibenzoylmethane, oxybenzone, octocrylene, menthyl anthranilate, 2-(2-hydroxy-5-methylphenyl) benzotriazole, 2-ethylhexyl (dimethoxybenzylidene dioxoimidazolidine) propionate; 2-phenylbenzimidazole-5-sulfonic acid, and 2-cyano-3,3-diphenyl acrylate.

Examples of the medicinal component may include the following. Examples of the vitamin may include vitamin As, such as coenzyme Q10, vitamin A oil, and retinol; vitamin B2s, such as riboflavin; vitamin B6s, such as pyridoxine hydrochloride; vitamin Cs, such as L-ascorbic acid, L-ascorbic acid magnesium phosphate, L-ascorbic acid monopalmitate, L-ascorbic acid dipalmitate, and L-ascorbic acid-2-glucoside; pantothenic acids, such as calcium pantothenate, vitamin Ds, such as vitamin D2 and cholecalciferol; and vitamin Es, such as α-tocopherol, tocopherol acetate, and DL-α-tocopherol nicotinate.

Examples of the whitening agent may include arbutin, ellagic acid, tranexamic acid, placenta extract, glutathione, and saxifrage extract.

Examples of the skin activator may include royal jelly and beech tree extract.

Examples of the blood circulation promoting agent may include capsaicin, zingerone, canthari tincture, ichthammol, caffeine, tannic acid, and γ-oryzanol.

Examples of the anti-inflammatory agent may include glycyrrhizic acid derivatives, glycyrrhetinic acid derivatives, azulene, and alitein.

Examples of amino acids include arginine, serine, leucine, and tryptophan.

Examples of various extracts may include horse chestnut seed extract, chamomile flower extract, mulberry bark extract, peony extract, parsley extract, beech tree extract, wine yeast extract, grapefruit extract, *Lonicera japonica* extract, rice extract, grape extract, hop extract, rice bran extract, loquat extract, Phellodendron amurense extract, coix seed extract, *Swertia japonica* extract, melilot extract, perch extract, licorice extract, peony extract, *Saponaria officinalis* extract, loofah extract, capsicum extract, lemon extract, *Gentiana lutea* extract, perilla extract, aloe extract, rosemary extract, sage extract, cinnamon bark extract, thyme extract, tea extract, seaweed extract, cucumber extract, clove extract, carrot extract, Horse chestnut extract, hamamelis extract, mulberry extract, scutellaria root (okugon) extract, hypericum erectum, quickthorn extract, *Centella asiatica* extract, Pueraria plant root nodule extract, artichoke leaf extract, rose fruit extract, and edelweiss extract.

Examples of preferred types of makeup cosmetics of the present invention may include foundations and makeup bases. The foundations may have forms of, for example, loose foundations, cake powder foundations, W/O emulsion liquid foundations, and oil-based stick foundations. The makeup bases may have forms of W/O emulsion makeup bases, O/W emulsion makeup bases, and the like.

Since a makeup cosmetic of the present invention contains the yeast cell wall particles, the makeup cosmetic has a soft focus effect, a skin beautifying effect, and a moisture retaining effect that are excellent and are effects particularly expected in makeup cosmetics. Furthermore, the makeup cosmetic of the present invention can contain the yeast cell wall particles as a main component of its powder components, and can be a makeup cosmetic that is safe and enables reduction in environmental impact.

EXAMPLES

Hereinafter, the present invention will be described specifically with reference to examples; however, the technical scope of the present invention is not limited to the following examples.

Production Example 1

As described below, yeast cell wall fraction particles were prepared by decolorization, delipidation, and drying of a yeast cell wall fraction from which intracellular components had been removed.

A commercially available yeast (*Candida utilis*) was used as a raw material A. An extract was extracted from the yeast of the raw material A with hot water, and a residue (solid content) after the extraction was recovered to be prepared as a cell wall fraction. A solution containing the cell wall fraction at a concentration of 5% and adjusted to be at a pH of 11.5 with an aqueous solution of 48% sodium hydroxide had hydrogen peroxide added thereto so that the content of hydrogen peroxide in the solution became 1%, and then stirred for 20 hours in a water bath adjusted to be at a temperature of 60° C. to undergo a decolorization reaction. After the decolorization reaction, the pH was adjusted to 7.0 with 1N HCl, and for removal of hydrogen peroxide remaining therein, catalase (product name: Leonet F Plus, manufactured by Nagase ChemteX Corporation) was added to be 1% of the hydrogen peroxide, and then a reaction was conducted for 30 minutes. After catalase remaining therein had been inactivated, centrifugation (8,000 rpm, 10 min) was performed, and the residue was washed with water three times. The residue was then suspended in water so as to be at a concentration of 5% again, and washing was performed by stirring for 20 hours in a water bath adjusted to a temperature of 28° C. After being washed with water three times in the same manner, the residue was suspended in ethanol so that the concentration of the residue became 5%, and the suspension was left still for 20 hours in a water bath adjusted to a temperature of 28° C. so that the suspension was delipidated. The delipidated suspension was centrifuged (8,000 rpm, 10 min), and the residue was washed with water three times. Spray drying was performed thereafter with a spray dryer (manufactured by Tokyo Rikakikai Ltd.), thus obtaining a white powder (Production Example 1).

Production Example 2

The process described in Production Example 1 was repeated twice, the process being from the extraction of an extract from yeast with hot water, through the centrifugation after the delipidation, to the washing of the residue with water three times. Spray drying was thereafter performed with the spray dryer (manufactured by Tokyo Rikakikai Co., Ltd.), thus obtaining a white powder (Production Example 2).

Production Example 3

A white powder (Production Example 3) was obtained in the same manner as in Production Example 2, except that: yeast (*Candida utilis*) cultured in a spent sulfite liquor served as a raw material B; component extraction from the yeast of the raw material B was performed by extraction with hot solution of sodium chloride, and a residue (solid content) recovered after the extraction was used; and a decolorization reaction was conducted with 0.1 N aqueous sodium hydroxide solution.

Figure 2:
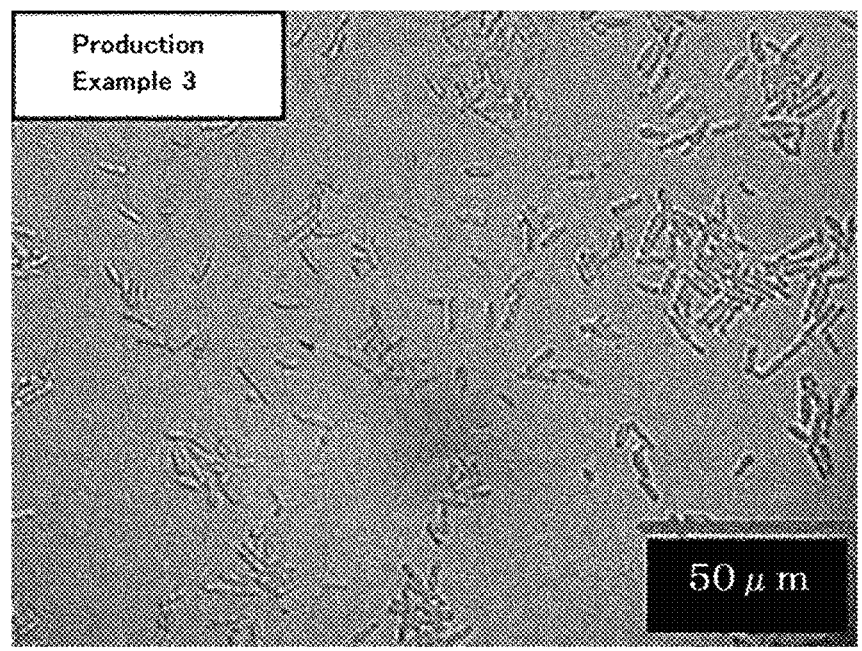
FIG. 2 is a micrograph of yeast cell wall fraction particles of Production Example 3.

Electron micrographs (manufactured by Keyence Corporation) of the obtained white powders (yeast cell wall fraction particles) were taken. FIGS. 1 and 2 are respectively micrographs of Production Examples 1 and 3.

Evaluation Method

The white powder (yeast cell wall fraction particles) obtained in Production Example 1 was evaluated with respect to the following items.

Yield

The weight of the residue (a yeast cell wall fraction sample), which had been delipidated and washed with water and was yet to be subjected to spray drying, was divided by the weight of viable cells of yeast used as the raw material (the weight of yeast input), and the yield (%) was thereby obtained as a percentage.

Particle Size Distribution and Average Particle Diameter

A laser diffraction particle size distribution measuring device (Mastersizer 3000, manufactured by Malvern) was used. Water was used as a dispersion medium for measurement, and 0.1 g of each sample was added. The measurement was performed to determine a particle size distribution and a particle diameter at a cumulative total of 50% (an average particle diameter).

Whiteness

Reflectance of the obtained powders was measured as whiteness of the obtained powders by used of a spectral color difference meter SE6000 manufactured by Nippon Denshoku Industries Co., Ltd.

β-Glucan Content

β-glucan content was measured using a β-glucan measurement kit (manufactured by Megazyme) according to a manual pertaining thereto.

It was confirmed that the β-glucan content values of Production Example 1 and Production Example 2 were increased as compared with the yeast serving as their raw material.

Figure 3:
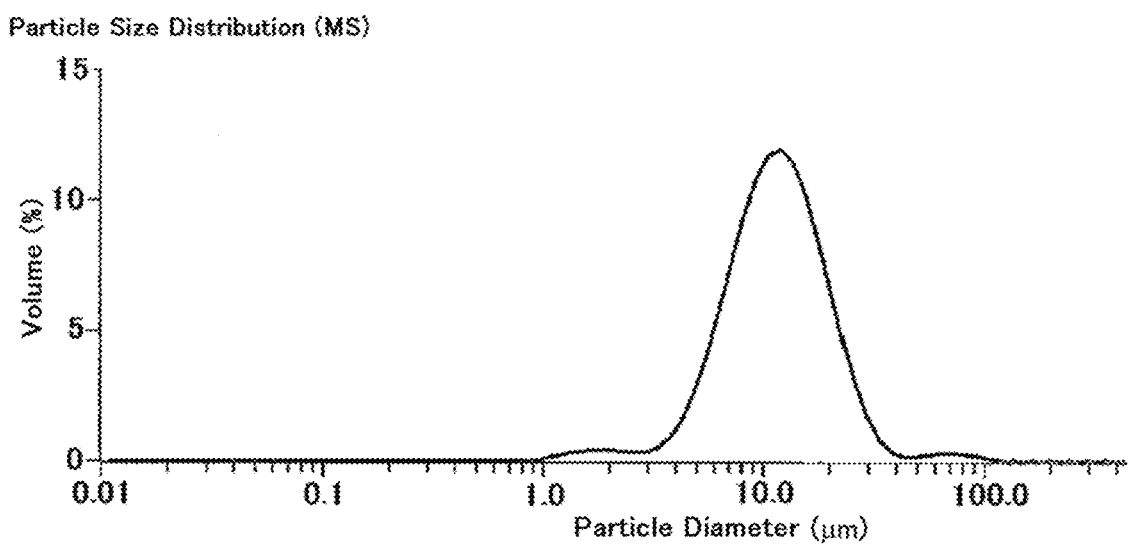
FIG. 3 is a diagram depicting a particle size distribution of the yeast cell wall fraction particles of Production Example 1.

Table 1 has, listed therein, results for each item measured with respect to the white powders of Production Examples 1 to 3 according to the above-described measurement methods. FIG. 3 depicts the particle size distribution of the white powder of Production Example 1.

TABLE 1

| | Measurement Results | | | |
|---|---|---|---|---|
| | Yield [%] | Whiteness | β-glucan content [%] | Average particle diameter [µm] |
| Production Example 1 | 27.0 | 87.59 | 24.9 | 10.2 |
| Production Example 2 | 6.9 | 87.78 | 65.8 | 12.2 |
| Raw Material A | — | 75.86 | 12.2 | 48.4 |
| Production Example 3 | 56.7 | 81.98 | 6.09 | 7.92 |
| Raw Material B | — | 65.47 | 6.85 | 13.6 |

Examples 1 to 4: Foundation

Foundations were prepared as follows. A commercially available powder foundation (AC Powdery Foundation, Medium Beige, manufactured by Do-Best, Inc.) and the white powder obtained in Production Example 1 were blended in ratios (parts by weight) of 95:5 (Example 1), 90:10 (Example 2), and 80:20 (Example 3), respectively; a small amount of 70% by weight ethanol was added to the mixtures and mixed well in a mortar; the mixtures were then dried overnight in a drying machine at 40° C.; and foundations of Examples 1 to 3 were thereby obtained. Furthermore, the above-mentioned commercially available powder foundation and the white powder obtained in Production Example 3 were blended in a ratio (parts by weight) of 80:20 (Example 4); a small amount of 70% ethanol was added to the mixture and mixed well in a mortar; the mixture was then dried in a drying machine overnight at 40° C.; and a foundation of Example 4 was thereby obtained.

Comparative Example 1: Foundation

A foundation of Comparative Example 1 was obtained in the same manner as in Example 1, except that the white powder obtained in Production Example 1 was not added to the commercially available powder foundation (manufactured by Do-Best, Inc.).

Comparative Example 2: Foundation

The above-mentioned commercially available powder foundation and commercially available microbeads (manufactured by Sumitomo Seika Chemicals Co., Ltd., having an average particle diameter of 182 µm) were blended in a ratio of 80:20 (parts by weight); a small amount of 70% ethanol was added to the mixture and mixed well in a mortar; the mixture was then dried in a drying machine overnight at 40° C.; and a foundation of Comparative Example 2 was thereby obtained.

Evaluation of Soft Focus Effect

Soft focus effects were evaluated according the following evaluation criteria by visual observation of inconspicuousness of unevenness (soft focus effects). Artificial leather, Supra Le (manufactured by Idemitsu Fine Techno), was cut into pieces having a size of 5 cm×10 cm, and 25 mg of the foundations of Examples 1 to 4 and Comparative Examples 1 and 2 were applied to the cut pieces by use of cosmetic sponges; and were thereafter visually evaluated by use of photographs taken at a magnification of 35 times by a digital microscope (Digital Microscope KH-8700 manufactured by Hirox Co., Ltd.). Table 2 has results of the visual evaluation listed therein. Furthermore, FIG. 4 has photographs for comparison among Examples 1 to 4, Comparative Examples 1 and 2, and a blank. The blank is the artificial leather having nothing applied thereon.

Evaluation Criteria
A: Very good
B: Good
C: Normal
D: Poor

Those that met the criteria A to C were determined to be at practical levels.

TABLE 2

Results of Evaluation for Soft Focus Effects

|  | Visual Evaluation |
|---|---|
| Example 1 | C |
| Example 2 | B |
| Example 3 | A |
| Example 4 | B |
| Comparative Example 1 | D |
| Comparative Example 2 | D |

Figure 4:
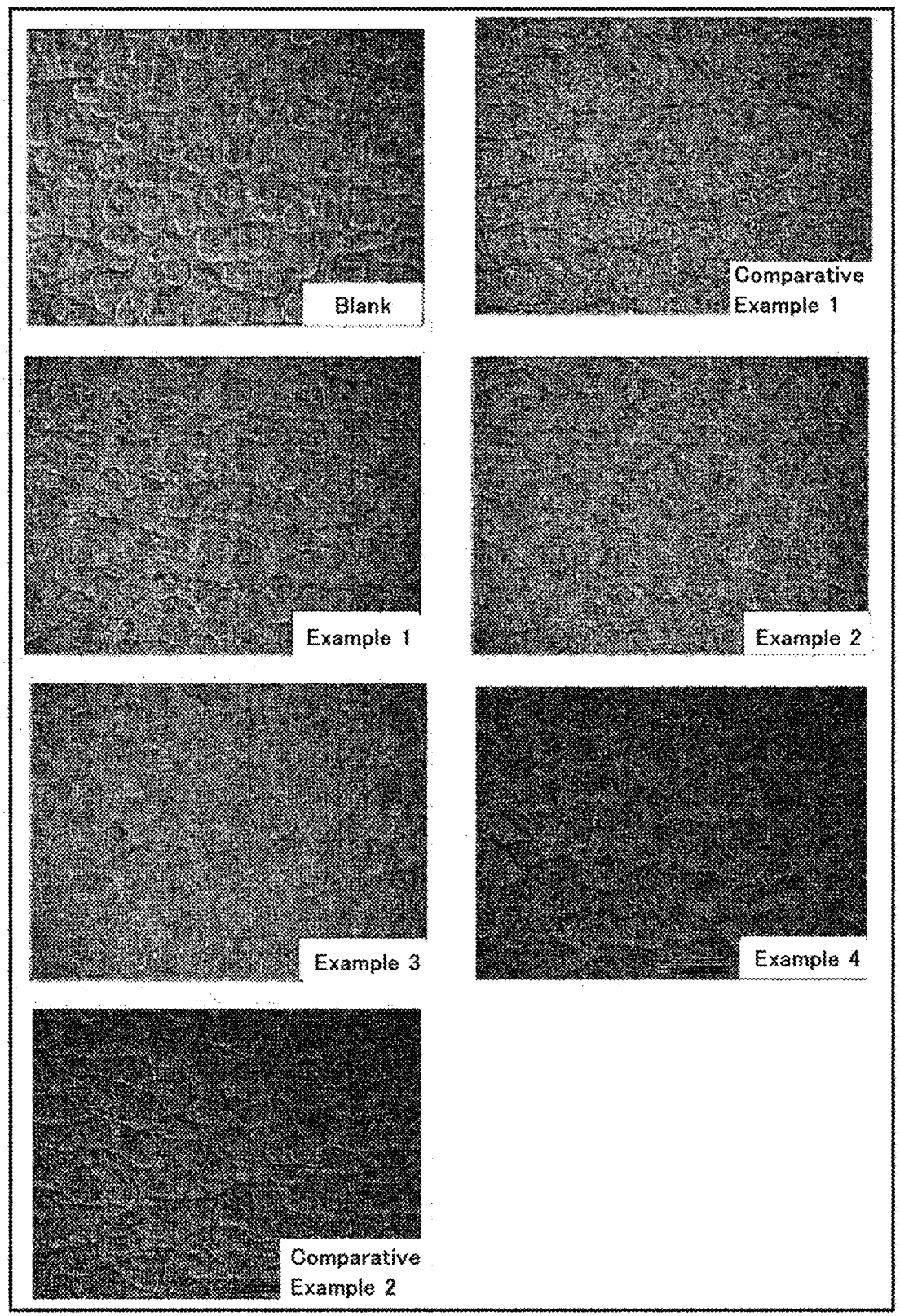
FIG. 4 is a diagram for comparison among photographs of leather surfaces that underwent evaluation tests for soft focus effects of Examples and Comparative Examples.

From the results in Table 2 and FIG. 4, unevenness in a grained pattern appeared blurred on the artificial leather pieces coated with the foundations of Examples 1 to 4 as compared with the blank and Comparative Example 1, and it has thus been found that the foundations of Examples 1 to 4 had soft focus effects.

Evaluation of Light Scattering Effect

Wheat flour, the yeast cell wall particles of Production Example 1, and two types of silicon-acrylic fine particles used for light diffusion of cosmetics were prepared as powder samples 1 to 4 below, and goniophotometric measurement was performed to evaluate their light scattering effects.

Powder sample 1: wheat flour (soft flour of wheat, "Nisshin Cooking Flower", manufactured by Nisshin Flour Milling Inc.)

Powder sample 2: the yeast cell wall particles of Production Example 1

Powder sample 3: Tospearl 145 (Tanac Co., Ltd., average particle diameter: 4.5 μm, refractive index: 1.42 to 1.43, coefficient of variation (CV value): 10 to 15%)

Powder sample 4: Tospearl 120 (Tanac Co., Ltd, average particle diameter: 2.0 μm, refractive index: 1.42 to 1.43, coefficient of variation (CV value): 10 to 15%)

A base sample 1 (powder sample 1) and measurement samples 2 to 4 were prepared respectively for the powder samples 1 to 4 for measurement of values, such as reflectances, for the powder samples 1 to 4 by use of a goniophotometer. The measurement samples were each prepared by pasting an optical adhesive onto a black acrylic plate, sprinkling a sufficient amount of the powder sample on the adhesive layer, blowing off the excess with air, and forming a flat layer of the powder sample on one surface of the black acrylic plate.

The goniophotometer and the measurement conditions were as follows.

Goniophotometer: GC5000L (manufactured by Nippon Denshoku Industries Co., Ltd.)
Mode: reflection mode
Incident angle: 20° or 60°
Light receiving angle (reflection angle): −85° to 85°

A plane of each measurement sample was illuminated with light at an incident angle of 20° or 60°, and a reflectance distribution diagram was generated based on reflection intensities at respective light receiving angles while the light receiving angle was changed at 5° intervals in the range of −85° to 85°.

Figure 5:
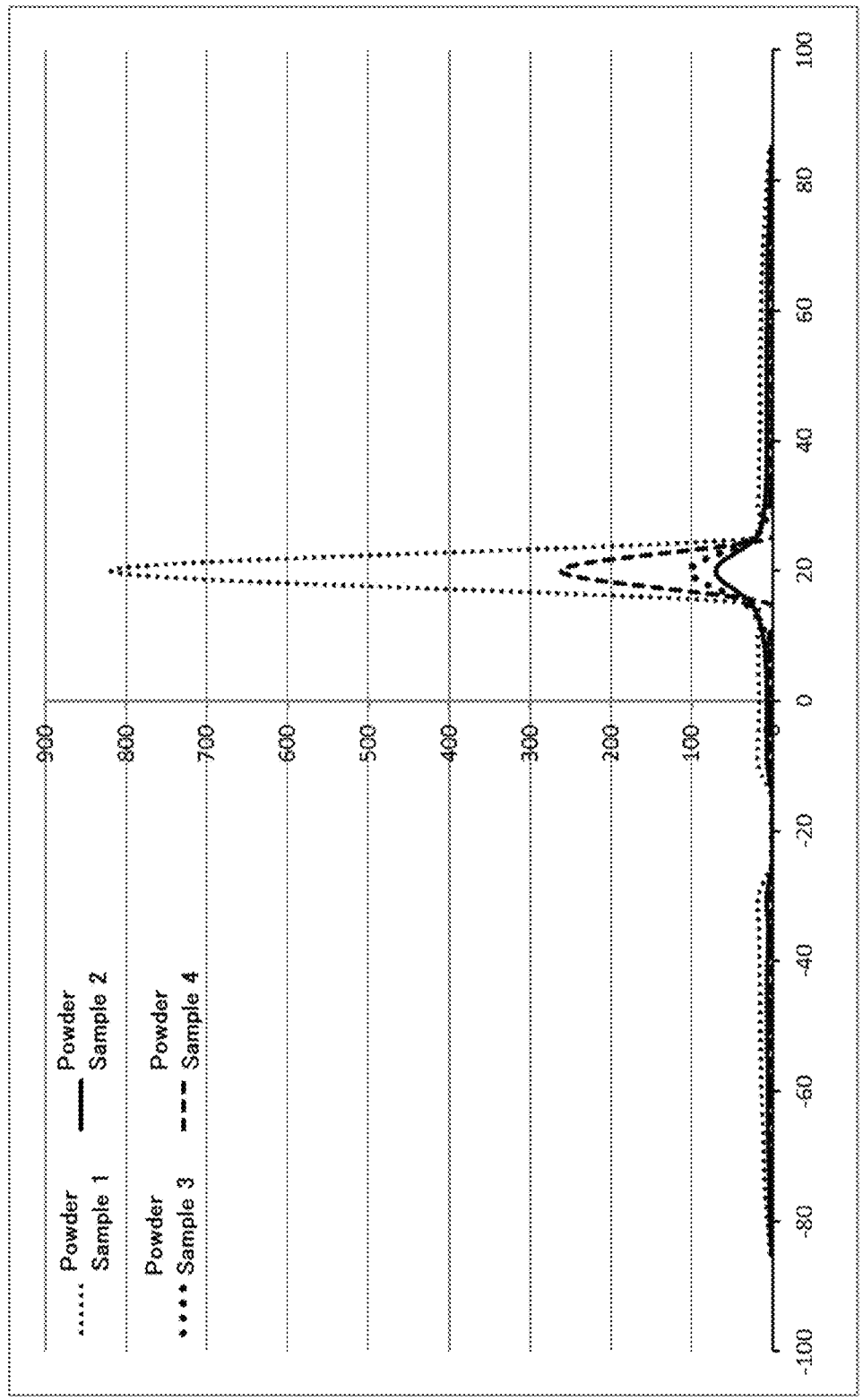
FIG. 5 is a diagram depicting a result of measurement of reflectance distribution diagrams of flat layers formed by use of powder samples 1 to 4, at an incident angle of 200.
Figure 6:
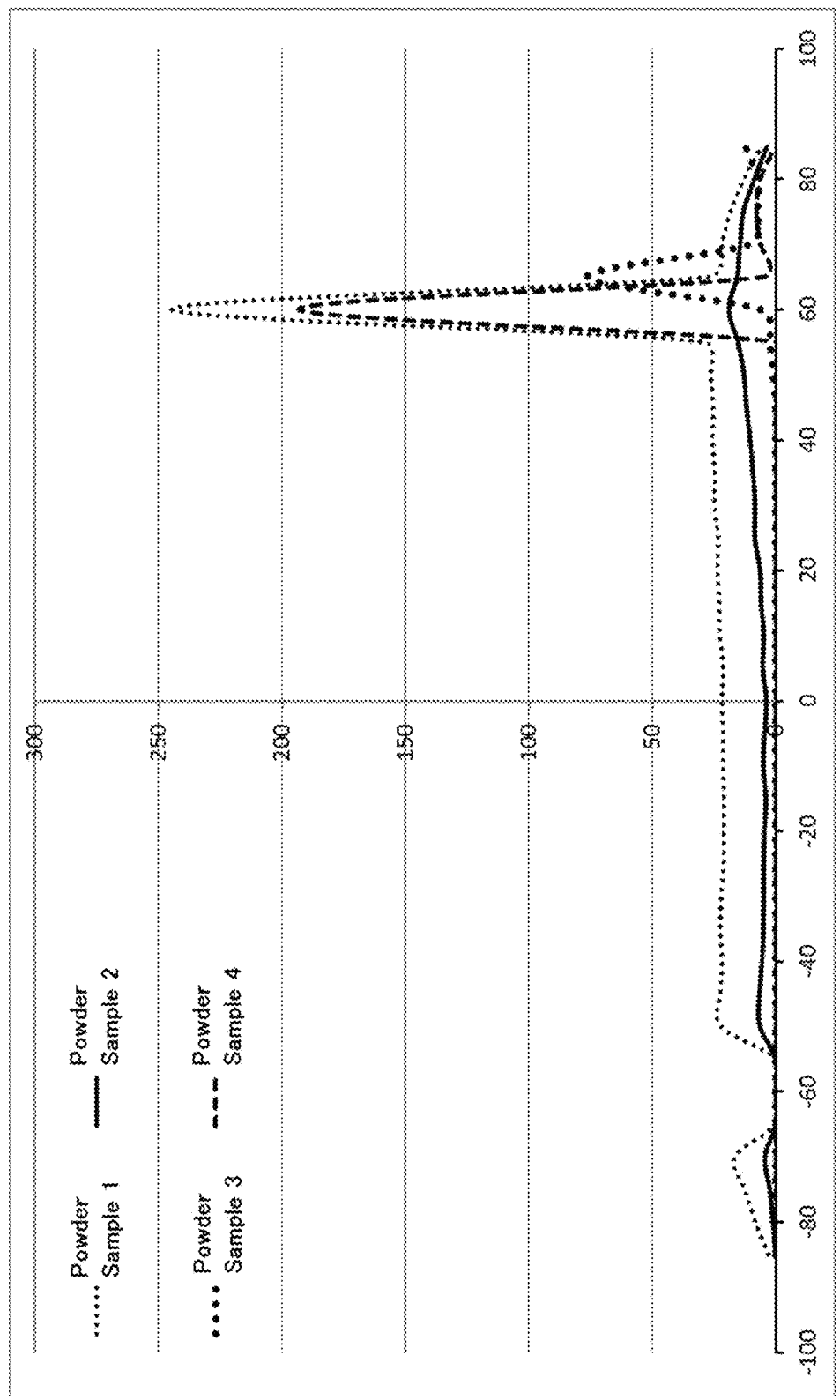
FIG. 6 is a diagram depicting a result of measurement of reflectance distribution diagrams of flat layers formed by use of the powder samples 1 to 4, at an incident angle of 600.

FIG. 5 is a reflectance distribution diagram at the incident angle of 20°, and FIG. 6 is a reflectance distribution diagram at the incident angle of 60°. In FIGS. 5 and 6, the horizontal axis represents the reflection angle, "0" thereon indicates the direction perpendicular to the plane of the measurement sample, and "90" thereon indicates the horizontal direction. The vertical axis represents the intensity of reflected light.

Reflectances were measured based on the obtained reflection intensities. With the reflection intensity of the base sample (powder sample 1) at each incident angle serving as a reference, the reflectance of each of the measurement samples 2 to 4 at each angle was determined by Equations (1) and (2) below. The reflectances determined are listed in Table 3.

$$\text{Reflectance } A \text{ (\%) at the incident angle of } 20° = \\ (100 \div \text{the reflection intensity of the base sample at the light receiving angle of } 20°) \times \text{the reflection intensity of each measurement sample at the light receiving angle of } 20° \quad \text{Equation (1)}$$

$$\text{Reflectance } A \text{ (\%) at the incident angle of } 60° = \\ (100 \div \text{the reflection intensity of the base sample at the light receiving angle of } 60°) \times \text{the reflection intensity of each measurement sample at the light receiving angle of } 60° \quad \text{Equation (2)}$$

TABLE 3

| | | Reflectance | | | |
|---|---|---|---|---|---|
| | | Base sample (Powder sample 1) | Measurement sample 2 (Powder sample 2) | Measurement sample 3 (Powder sample 3) | Measurement sample 4 (Powder sample 4) |
| Incident angle of 20° | Reflection intensity | 818.60 | 70.10 | 102.30 | 262.20 |
| | Reflectance [%] | — | 8.56 | 13.08 | 32.03 |
| Incident angle of 60° | Reflection intensity | 244.40 | 21.90 | 76.40 | 193.10 |
| | Reflectance [%] | — | 8.96 | 31.26 | 79.01 |

It was confirmed that the reflection patterns differed among the powder samples. In terms of the soft focus effect, the reflectance is considered to be preferably not high. Among the above powder samples, the powder sample 2 (the yeast cell wall particles of Production Example 1) has the lowest reflectance. In addition, as can be seen from FIG. 6 (when the incident angle is 60°), it can be deduced that the yeast cell wall particles of Production Example 1 are not too high in reflectance and enable adequate scattering.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cosmetic composition comprising:
    yeast cell wall particles retaining shapes of yeast cell walls and having an average particle diameter ranging from 3 to 25 µm, wherein
    a planar shape of the yeast cell wall particle retains an oval shape,
    the yeast cell wall particle is a cell wall fraction that has intracellular components of yeast removed, and
    an amount of the yeast cell wall particles in the composition ranges from 15% by weight to 90% by weight.

2. The cosmetic composition according to claim 1, wherein
    when a flat layer is formed of the cosmetic composition, the flat layer has a reflectance satisfying one or both of:
    a condition (a) where the reflectance is 30% or less at an incident angle of 20°; and
    a condition (b) where the reflectance is 30% or less at an incident angle is 60°.

3. The cosmetic composition according to claim 1, wherein the cosmetic composition is a makeup cosmetic material.

4. The cosmetic composition according to claim 1, wherein the cosmetic composition is a powder cosmetic material.

5. A method of using a powder composition, comprising:
    applying the powder composition on an object, thereby enhancing a soft focus effect, wherein
    the powder composition contains yeast cell wall particles retaining shapes of yeast cell walls,
    an average particle diameter of the yeast cell wall particle ranges from 3 to 25 µm,
    a planar shape of the yeast cell wall particle retains an oval shape,
    the yeast cell wall particle is a cell wall fraction that has intracellular components of yeast removed, and
    an amount of the yeast cell wall particles in the powder composition ranges from 15% by weight to 90% by weight.

6. The method of using a powder composition according to claim 5, wherein
    when a flat layer is formed of the powder composition, the flat layer has a reflectance satisfying one or both of:
    a condition (a) where the reflectance is 30% or less at an incident angle of 20°; and
    a condition (b) where the reflectance is 30% or less at an incident angle is 60°.

7. The method of using a powder composition according to claim 5, wherein the powder composition is a cosmetic composition.

8. The method of using a powder composition according to claim 5, wherein the object is a human.

9. The method of using a powder composition according to claim 5, wherein the object is human skin.

10. A method of enhancing a soft focus effect, comprising:
    applying a powder composition on an object, wherein
    the powder composition contains yeast cell wall particles retaining shapes of yeast cell walls,
    an average particle diameter of the yeast cell wall particle ranges from 3 to 25 µm,
    a planar shape of the yeast cell wall particle retains an oval shape,
    the yeast cell wall particle is a cell wall fraction that has intracellular components of yeast removed, and
    an amount of the yeast cell wall particles in the powder composition ranges from 15% by weight to 90% by weight.

11. The method of enhancing a soft focus effect according to claim 10, wherein
    when a flat layer is formed of the powder composition, the flat layer has a reflectance satisfying one or both of:
    a condition (a) where the reflectance is 30% or less at an incident angle of 20°; and
    a condition (b) where the reflectance is 30% or less at an incident angle is 60°.

12. The method of enhancing a soft focus effect according to claim 10, wherein the powder composition is a cosmetic composition.

13. The method of enhancing a soft focus effect according to claim 10, wherein the object is a human.

14. The method of enhancing a soft focus effect according to claim 10, wherein the object is human skin.

* * * * *